(12) United States Patent
Stoelwinder et al.

(10) Patent No.: US 9,096,552 B2
(45) Date of Patent: Aug. 4, 2015

(54) PROCESS FOR THE PREPARATION OF CONDENSATION PRODUCTS OF MELAMINE

(75) Inventors: Christiaan Johannes Cornelis Stoelwinder, Echt (NL); Gerard Jan Kwant, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/007,075

(22) PCT Filed: Mar. 27, 2012

(86) PCT No.: PCT/EP2012/055386
§ 371 (c)(1),
(2), (4) Date: Dec. 16, 2013

(87) PCT Pub. No.: WO2012/130827
PCT Pub. Date: Oct. 4, 2012

(65) Prior Publication Data
US 2014/0155599 A1      Jun. 5, 2014

(30) Foreign Application Priority Data
Mar. 28, 2011   (EP) .................................... 11159957

(51) Int. Cl.
*C07D 251/70* (2006.01)
*C07D 403/12* (2006.01)
*C07D 251/54* (2006.01)

(52) U.S. Cl.
CPC ............ *C07D 251/54* (2013.01); *C07D 251/70* (2013.01); *C07D 403/12* (2013.01)

(58) Field of Classification Search
CPC ............................ C07D 251/70; C07D 403/12
USPC .................................................. 544/198, 203
See application file for complete search history.

(56) References Cited

U.S. PATENT DOCUMENTS 5,985,960 A * 11/1999 de Keijzer et al. ............ 524/100

FOREIGN PATENT DOCUMENTS

| GB | 1 256 178 | 12/1971 |
| WO | WO 96/16948 | 6/1996 |

OTHER PUBLICATIONS

Lotsch et al., "New light on an old story: Formation of melam during thermal condensation of melamine", *Chemistry—A European Journal*, vol. 13, No. 17, 200, pp. 4956-4968.
Gavrilova et al., "Synthesis of Melam and its salts with mineral acids", *Journal of Organic Chemistry of the USSR*, vol. 13, Mar. 1, 1977, p. 616.
Gal'Perin et al., "Synthesis of Melam from melamine", *Journal of Organic Chemistry of the USSR*, vol. 7, Jan. 1, 1971, pp. 2524-2525.
International Search Report for PCT/EP2012/055386, mailed May 21, 2012.

* cited by examiner

*Primary Examiner* — Venkataraman Balasubramanian
(74) *Attorney, Agent, or Firm* — Nixon & Vanderhye P.C.

(57) ABSTRACT

The invention relates to a process for the purification of a melamine condensation product, comprising the steps of a) making a diluted slurry of a reaction product mixture comprising the melamine condensation product in a solution of a base in water with a pH of at least 9, b) keeping the diluted slurry for a period of at least 1 hour, c) concentrating the diluted slurry, thereby obtaining a concentrated slurry and an eluent, and d) washing the concentrated slurry by diluting the concentrated slurry with aqueous liquid and repeating step c, wherein the washing is performed by counterflow washing wherein eluents of downstream concentration steps are used to wash the slurry in upstream concentration steps.

11 Claims, 1 Drawing Sheet

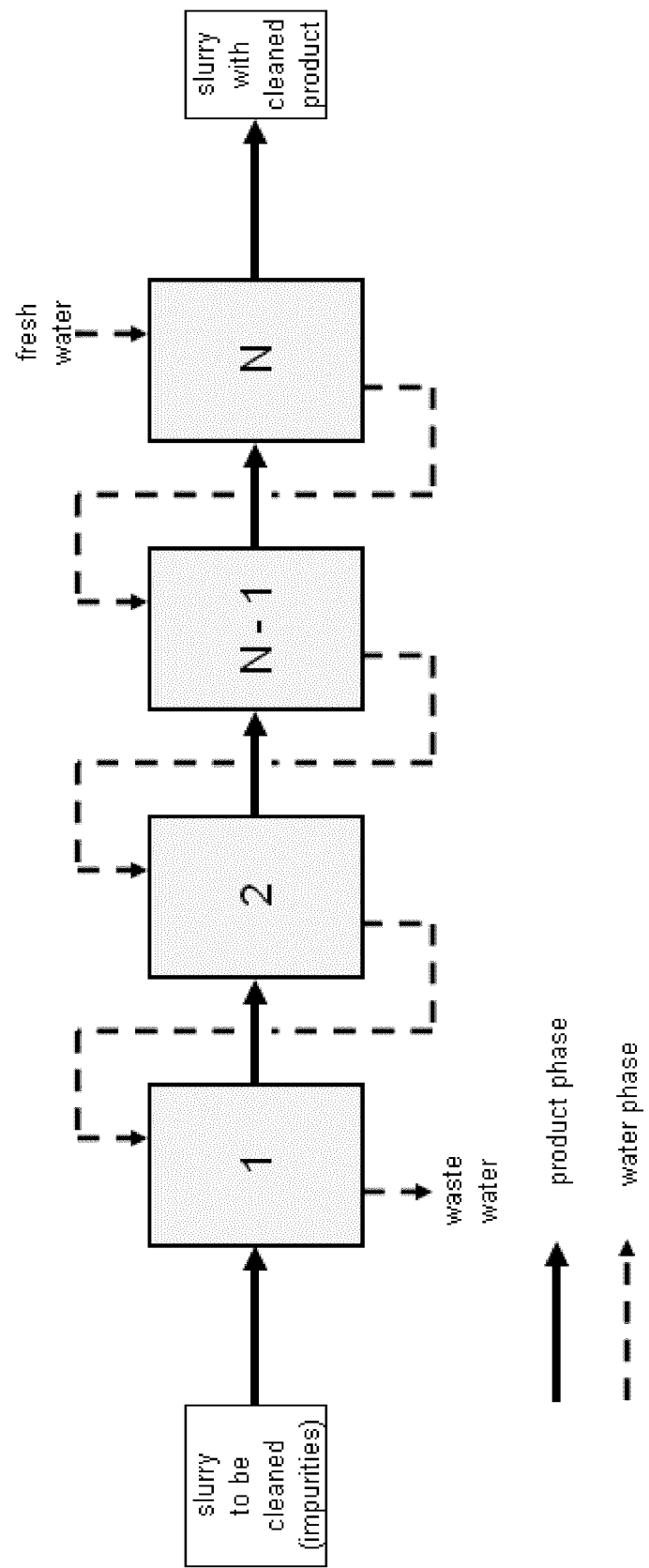

PROCESS FOR THE PREPARATION OF CONDENSATION PRODUCTS OF MELAMINE

This application is the U.S. national phase of International Application No. PCT/EP2012/055386 filed 27 Mar. 2012 which designated the U.S. and claims priority to EP 11159957.7 filed 28 Mar. 2011, the entire contents of each of which are hereby incorporated by reference.

The invention relates to a process for the preparation of a melamine condensation product, particularly melam.

Melamine forms melamine condensation products when heated under certain reaction conditions. Ammonia is evolved in the reaction. Similarly, melamine salts form condensation products when heated. Melamine condensation products include melem, melone, and melam, as well as salts thereof. Generally, melam ($C_6H_9N_{11}$) is formed upon heating melamine and/or melamine salts in the presence of a catalyst below 325° C. and is a by-product of melamine synthesis. Such a product is highly suitable for use as flame-proofing agents in polymer compositions. Melamine condensation products possess high thermal stability in comparison with other flame-proofing agents such as, for example, halogen compounds and melamine. Melam and higher melamine condensation products such as melem, melon and methone do not extensively sublime and decompose at temperatures below 350° C. As a result, the polymer compositions exhibit better thermal stability compared to compositions incorporating conventional flame proofing agents. A further advantage is that the formation of mold deposits during injection molding of the melam-filled polymer compositions is suppressed.

Specific processes relating to the preparation of melam via condensation are described in, for example, V. A. Gal'perin et al., Zhurnal Oraanicheskoi Khimii, Vol. 7, No. 11, pp. 2431-2432 (Nov. 1971) and Gavrilova et al. and in Zhurnal Oraanicheskoi Khimii, Vol. 13, No. 3, pp. 669-670 (Mar. 1977). In laboratory scale experiments, melamine was converted to a salt of melam with use of a ZnCl2 condensation agent at a temperature between 290° C. and 320° C.

The percentages of zinc and chloride in the melam product so obtained are very high. The presence of zinc and chloride impurities is a significant drawback for the use of the melam as a flame retardant in plastics. Both ions are difficult to wash out. Furthermore, washing zinc and chloride out of the product can result in a high degree of hydrolysis of the melam.

Alternatively, melamine can also be converted to a condensation product like melam on a laboratory scale (e.g. milligram or gram scale) in the presence of inorganic acids as condensation agents. Inorganic acids include HCl, HBr, sulfuric acid, phosphoric acid, and mixtures thereof. The ammonia or melamine salts of these acids can also be used.

A process providing a melamine condensation product is disclosed in WO 96/16948. This process comprises the step of heating a starting material comprising melamine or a melamine salt in the presence of:
  (i) at least one organic acid, or
  (ii) at least one ammonia or melamine salt of the organic acid, or
  (iii) a combination of (i) and (ii),
  under reaction conditions effective for the formation of melamine condensation product.

This process is suitable for commercial scale production.

Although the process of WO 96/16948 shows an improvement in view of the processes known before, a problem however with this process is that it is still difficult to obtain a melamine condensation product with a high level of purity. It results in a reaction product mixture comprising melamine condensation product and the organic or inorganic acid and/or salts or other residues thereof.

In the examples of WO 96/16948 a method is disclosed of washing the reaction mixture after the heating step with a solution of ammonia in water. Low levels of organic acid in the final mixture containing the condensation product are reported, after washing of, for example 420 g reaction mixture with only 1 liter of 3% aqueous ammonia. However, these findings are wrong, as only washing the reaction mixture after the heating step as indicated in WO 96/16948 does not provide the desired low level of organic acid in the final mixture containing the condensation product. As observed by the inventors, such low levels of impurities would require much larger amounts of washing liquids and more severe measures.

In a scientific article by V. B. Lotsch et al, Chem. Eur. J, 2007, 13, 4956-4968, the preparation of a melam hydrate is descibed. The melam hydrate was obtained from a melam-NH4Cl adduct, that was synthesized by heating melamine and NH4Cl (ammonium chloride) for 12 hours at 723 K (382° C.). The obtained melam-NH4Cl adduct (550 mg) was stirred in aqueous NH3 (60 mL, 25%).

In WO 96/16948, referred to above, experiments are described wherein melam is also prepared by reaction of melamine (25.2 g) with ammonium chloride (5.4 g). The mixture was heated for 2 hours at 340° C. The product was washed with one liter of a 3% ammonia solution. The yield of melam was 90% and the residual chloride content was 5.7%.

Apparently such low concentration solutions in combination with a lower amount of washing liquid are not efficient in removing residual acid components from the melam. Despite the use of still relative large volumes of water for washing, does not lead to a high purity. Large amounts of highly concentrated ammonia showed to be effective and might be useful for purifying such a small amount of melam for scientific studies, but is not suitable for use on industrial scale.

Object of the invention is therefore to provide a process that can be applied on industrial scale wherein readily a high purity of the final mixture containing the melamine condensation product is obtained.

Surprisingly this object is obtained with a purification process of a melamine condensation product, for example obtained by a process comprising the step as defined above, wherein the purification process comprises the steps of:
  a) making a diluted slurry of a reaction product mixture comprising the melamine condensation product in a solution of a base in water with a pH of at least 9,
  b) keeping the diluted slurry for a period of at least 1 hour,
  c) concentrating the diluted slurry, thereby obtaining a concentrated slurry and an eluent, and
  d) washing the concentrated slurry by diluting the concentrated slurry with aqueous liquid and repeating step c,
  wherein the washing is performed by counterflow washing wherein eluents of downstream concentration steps are used to wash the concentrated slurry in upstream concentration steps.

The effect of this purification process is that basic aqueous solutions with a relative low base concentration can be used and the overall amount of water needed is kept within reasonable limits, while surprisingly nevertheless a melamine condensation product with a relative high purity is obtained.

The process according to the invention suitably comprises multiple washing steps. The process has for example N washing steps, N being a positive integer. With a positive integer is meant all the whole numbers greater than zero: 1, 2, 3, 4, 5, etc. In this process according to claim 1, the washing of the concentrated slurry is preferably carried out in such a way that in step $n_1=x$, x being an integer (selected) from 1 up to and including N−1, the mixture is washed with water used in step $n_2=x+1$ and wherein in step $n_3=N$ the condensation product is washed with a fresh aqueous liquid, preferably water.

The number of washing steps N is at least 2, and preferably in the range of 2-10.

For the concentration step in the process according to the invention, to separate and obtain the concentrated slurry and the eluent from the diluted slurry, in principle any method that can be used in industrial scale processes may be applied. Such process may be done by filtration or sedimentation. These may be combined with centrifugation to speed up the process, such as in centrifugal filtration or in centrifugal sedimentation.

Washing can be accomplished by filtration or sedimentation techniques. Examples of such techniques include decanting centrifuge, cross flow filtration, centrifugal filtration, and static filtration. These technologies are combined with counterflow washing wherein eluents of downstream concentration steps are used to make the slurry in upstream concentration steps. Thus savings of wash waterliquid requirements of 75-85% can be achieved.

Preferably the concentration is done by cross flow filtration (micro filtration); centrifugal sedimentation (decanter centrifuge); centrifugal filtration (basket centrifuge) or dead end filtration (Nutsche or belt filter), each combined with counterflow washing.

Cross flow filtration (e.g. micro filtration) has the advantage that high filtration flux can be achieved and no cake is formed that can crack and corroborate the filtration process.

Centrifugal sedimentation (e.g. decanter centrifuge) has the advantage that the washing liquid does not need to penetrate a filter cake. The sediment is rather easily re-slurried with fresh waterliquid. Depending on the particle size, density and G-force the separation speed can be high.

Centrifugal filtration (e.g. basket centrifuge) allows for intensive wash-waterliquid/cake contact results in a high concentration factor and a low wash-waterliquid consumption.

Dead end filtration (e.g. Nutsche, Bchner or belt filter) also gives an intensive washwater filter cake contact, resulting in a high concentration factor. This results in a low wash waterliquid consumption.

Most preferred is dead-end filtration, combined with counterflow washing, which allow the lowest wash water requirements. Also most preferred is a sedimentation centrifuge combined with counterflow washing. This allows very low wash waterliquid requirements and a very stable process, with reduced risk of cake cracking resulting in inhomogeneous washing.

Preferably step b) of keeping the diluted slurry is carried out at a temperature between 20° C. and 70° C., more preferably between 30° C. and 60° C. Step b) is preferably carried out for e period of at least 2 hours, more preferably for a period of at least 4 hours. Step b) is preferably carried out for a period of at most 15 hours, more preferably at most 10 hours, even more preferably at most 8 hours, most preferably at most 6 hours. The pH of the solution of a base in water is preferably at least 9, more preferably at least 10, still more preferably at least 12, most preferably between 12 and 14. With pH of the solution is meant the pH of the starting solution, it is the solution before it is brought together with the reaction mixture to make the diluted slurry in the solution. Preferably the base is used in an amount of more than stoichiometric, more preferably at least more than 1.25 times of the stoichiometric amount in view of the inorganic or organic acid used in the heating step. As base it is possible to use, for example, ammonia, or an alkali hydroxide, such as sodium hydroxide or potassium hydroxide. Best results with respect of obtained purity in the final product are obtained with sodium hydroxide and potassium hydroxide.

Preferably the concentration of the solids in the diluted slurry is between 5 and 25 weight (wt) % of the total weight of the diluted slurry, more preferably between 10-18 wt. %.

Good results are obtained if a slurry of the mixture and the solution of the base are mixed in a stirred vessel and kept in the stirred vessel at the temperature and for the time period indicated above.

Preferably the steps a) of making a diluted slurry of the mixture and b) keeping the diluted slurry are directly carried out after the heating step, wherein the condensation product is formed, preferably with cooling of the mixture to a temperature below 100° C. before bringing the mixture into contact with the solution of the base.

After step b) of keeping the diluted slurry for a certain period of time at a certain temperature, the diluted slurry is concentrated. Result of such concentration is in most cases a concentrated cake of a mixture containing the condensation product. Such concentration may be carried out by using a filter, a basket centrifuge or a decanter centrifuge.

In case a filter or a basket centrifuge (dead end filteration) is used the concentrated slurry suitably is washed with water prior to removal of the concentrated slurry from the filter or the basket centrifuge.

In case a decanter centrifuge (sedimentation) is used washing is suitably carried out by mixing the concentrated slurry with water in a vessel to obtain a diluted slurry again, which diluted slurry is after the washing step concentrated to obtain a concentrated cake again. Suitably the washing is carried out with water, preferably at a temperature of 20-70° C.

Preferably the washing of the concentrated slurry is carried out by N washing steps, wherein in step $n=x$, x is an integer from 1 (the first washing step) up to and including N−1 (the washing step before the last washing step) the concentrated slurry is washed with water used in step $x+1$ and wherein in the final washing step N the condensation product is washed with fresh water.

A schematic reprentation of such a process is given in FIG. 1.

In this way the net water need is only a fraction of the amount if only fresh water is used in every washing step, so that a highly economical process is obtained.

As fresh water any water may be used, but preferably water with a low mineral content is used, such as for example drinking water, process water or demineralized water.

Preferably $N=2-10$, in other words N is an integer in the range of 2-10. More preferably $N=3-8$, most preferably $N=3-6$. In this way it is possible to use less than 50 liters of water per kg of purified condensation product. Preferably less than 30 liters of water are used per kg condensation product, more preferably less than 20 liters, most preferably less than 10 liters.

After the washing step the mixture may be dried.

The melamine condensation products of the present invention are the result of self-condensation of a starting material comprising melamine or melamine salt resulting in the evolution of ammonia. Exemplary melamine condensation products include melam, melem, and melone.

Preferably, the melamine condensation product comprises at least 90 weight % melam.

The amount of melamine condensation products is suitably determined by HPLC (=high pressure liquid chromatography).

Examples of melamine salts that may be used in the process according to the invention include salts prepared from phosphoric acid, sulfuric acid, nitric acid, fatty acids, and formic acid.

The heating step in the process of the present invention is carried out at temperatures and under reaction conditions that effect the formation of a melamine condensation product. For example, the heating step may be carried out such as to yield a maximum temperature between about 250° C. and about 350° C. By preference, however, the heating step is effectuated to yield a maximum temperature between about 260° C. and about 300° C.

Preferably, ammonia is removed from the reaction site as it is evolved.

The organic or the inorganic acid is used as condensation agent. As inorganic acid phosphoric acid, sulfuric acid and nitric acid may be used. Preferably an organic acid is used. The organic acid may be selected from a variety of organic acids.

In general, the organic acid can have, for example, a carboxylic, sulfonic, or phosphoric group in its structure. Other acidic groups are possible.

Very good results with the process according to the invention are obtained if the organic acid used is a sulfonic acid, more preferably para-toluene sulfonic acid, since a high level of purity is obtained.

In general, the amount of organic acid or salt of an organic acid may be, for example, between about 0.05 to about 5.0 mol relative to the amount of melamine or melamine salt. By preference, the amount of organic acid or salt of organic acid is between about 0.1 to about 3.0 mol relative to the amount of melamine or melamine salt.

The heating step is preferably effectuated while providing at least some agitation to the reaction mixture.

For example the reaction mixture may be stirred. By preference, the reaction is carried out in a stirred reactor that is virtually horizontally mounted. As a result of condensation, ammonia, $NH_3$, is formed. Ammonia can be purged from the reactor with use of an inert gas such as, for example, nitrogen. The length of the heating step may be 1-6 hours, by preference 3-5 hours.

The melamine condensation product such as melam can be mixed with polymers to yield flame-proof compositions. It has been found that melamine condensation products such as melam produced with the process according to the invention are highly suitable for use as flame proofing agents in polymer compositions.

Preferably by the process of the present invention a final mixture is obtained
containing the melamine condensation product and the organic acid, wherein the content of the organic acid in the mixture is less than 0.1 part by weight (pbw) at 100 pbw of the condensation product, more preferably less than 0.05 pbw at 100 pbw of the condensation product.

The flame-proofed polymer compositions, e.g., at least flame retardant, may be prepared by mixing one or more polymers together with a melamine condensation product such as melam in, for example, an extruder at an elevated temperature of, for example, between about 150° C. to about 450° C. The mixture is transformed into granules (or other desired physical form, e.g. pellets, powders, flakes, etc.).

The relative amounts of melamine condensation product and moldable polymer are selected so that the final composition is provided with flame retardancy and moldability. The quantity of melamine condensation product may be, for example, between 5 and 35 wt. %, and preferably between 10 and 25 wt. %.

Pulverulent particles of the polymer compositions are preferred which are relatively uniform in composition. The transformation to a final physical form can be practiced in diverse manners as known to those skilled in the art.

Polymers which can be flame-proofed by means of the melamine condensation product are preferably moldable polymers. Preferably, the polymers can be injected molded and are thermoplastic polymers. In some cases, however, thermosetting polymers can also be used. Diverse polymers and mixtures of polymers can be used. Examples include one or more of the following polymers:

(1) Polymers of mono- and di-olefins, such as, for example, polypropylene (PP), polyisobutylene, poly-(butene, polymethyl-1-pentenes, polyisoprene, polybutadiene, polyethylene (optionally crosslinked), such as, for example, high-density polyethylene (HDPE), low density polyethylene (LDPE) or linear low-density polyethylene (LLDPE) or mixtures thereof;

(2) Copolymers of mono- and di-olefins, optionally with other vinyl monomers, such as, for example, ethylene-propylene copolymers, linear low-density polyethylene and mixtures of these with low-density polyethylene, as well as terpolymers of ethylene with propylene and a diene such as hexadiene, dicyclopentadiene or ethylidene norbornene (EPT); further, mixtures of such copolymers with the polymers described under (1), such as, for example, polypropylene/ethylene-propylene copolymers;

(3) Polystyrene, poly(p-methylstyrene), poly(amethylstyrene) and copolymers of styrene or amethylstyrene with dienes or acryl derivatives, such as, for example, styrene butadiene, styrene acrylonitrile, styrene alkylmethacrylate, styrene butadiene alkylacrylate, styrene-maleic anhydride, styrene-acrylonitrile-methylacrylate, as well as block copolymers of styrene, such as, for example, styrene-butadiene-styrene, styrene-isoprene-styrene, styrene-ethylene/butylene-styrene or styreneethylene/propylene-styrene;

(4) Graft copolymers of styrene or a-methylstyrene on polybutadiene, polybutadiene-styrene or polybutadiene-acrylonitrile copolymers; styrene and acrylonitrile (or methacrylonitrile) on polybutadiene (ABS); styrene, acrylonitrile and methylmethacrylate on polybutadiene (xBS); styrene and maleic anhydride on polybutadiene; styrene, acrylonitrile and maleic anhydride or maleic acid imide on polybutadiene; styrene and maleic acid imide on polybutadiene; styrene and alkyl acrylate (or alkyl methacrylate) on polybutadiene; styrene and acrylonitrile on ethylene-propylene-diene terpolymer (AES), polyalkyacrylate or polyalkylmethacrylate on acrylate-butadiene copolymer, as well as mixtures with the copolymers described under (3).

(5) Polymers derived from a,S-unsaturated acids and derivatives thereof, such as polyacrylates and polymethacrylates and polyacrylamide and copolymers thereof with other unsaturated monomers, such as, for example, acrylonitrile-butadiene copolymers, acrylonitrile-alkylacrylate copolymers, acrylonitrile-alkoxyalkylacrylate copolymers or acrylonitrile-alkylmethacrylate-butadiene terpolymers;

(6) Polymers derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine, as well as the copolymers with the olefines described under (1);

(7) Homopolymers and copolymers of cyclic ethers, such as polyalkylene glycols, polyethylene oxide, polypropylene oxide or their copolymers with bisglycidyl ethers;

(8) Polyacetals, such as polyoxymethylene, as well as such polyoxymethylenes containing comonomers such as, for example, ethylene oxide; polyacetals modified with thermoplastic polyurethanes, acrylates or NBS;
(9) Polyphenylene oxide and sulfide and their mixtures with styrene polymers or with polyamides;
(10) Polyurethanes derived from polyethers, polyesters and polybutadiene with terminal hydroxyl groups on the one hand and aliphatic or aromatic polyisocyanates on the other, as well as their precursor products;
(11) Polyamides and copolyamides which are derived from diamines and dicarboxylic acids and/or from amino carboxylic acids or the corresponding lactams, such as polyamide 4, polyamide 6/6, 6/10, 6/9, 6/12, 4/6, polyamide 11, polyamide 12, aromatic polyamides based on an aromatic diamine and adipic acid; polyamides made from hexamethylene diamine and isophthalic and/or terephthalic acid and optionally an elastomer as modification agent, for example, poly-2,4,4-trimethyl hexamethylene terephthalamide, poly-m-phenyleneisophthalamide; block copolymers of polyamides with polyolefins, oleo in copolymers, ionomers or chemically bound or grafted elastomers, or with polyethers such as, for example, with polyethylene glycol, polypropylene glycol or polytetramethylene glycol; further, polyamides or copolyamides modified with EPT or ABS, as well as polyamides formed during the processing (RIM polyamide systems);
(12) Polyureas, polyimides, polyamide imides, polybenzimidazols, and polysiloxanes;
(13) Polyesters derived from dicarboxylic acids and dialcohols and/or from hydroxycarboxylic acids or the corresponding lactones such as polyethylene terephthalate, polybutylene terephthalate, poly-1,4-dimethylolcyclohexane terephthalate, polyhydroxybenzoates, as well as block polyether esters derived from polyethers with hydroxyl end groups; further, polyesters modified with polycarbonates or MBS;
(14) Polycarbonates, polyester carbonates, polysulfones, polyether sulfones and polyether ketones; and
(15) Thermosetting resins such as, for example, unsaturated polyesters, saturated polyesters, alkyd resins, polyacrylates or polyethers or compositions comprising one or more of these polymers and a crosslinking agent.

The flame-proofed polymer compositions can also contain ingredients used in polymer compositions as known to those skilled in the art such as, for example, fillers, plasticizers, lubricants, stabilizers, flame retardants, synergists, processing aids, and reinforcing fibers such as carbon fibers or glass fibers.

EXAMPLES

The present invention will be illustrated by means of the following non-limiting examples.

Comparative Experiment A

A mixture of melamine (252 grams) (DSM) and para-toluene sulfonic acid monohydrate (174 grams) (Hoechst) was heated with stirring at a temperature of 290° C. in a 2-liter flask placed in an oven. Ammonia ($NH_3$) formed from the condensation reaction and was removed from the reaction mixture by means of nitrogen. The ammonia was trapped with a 1 molar $H_2SO_4$ solution. After a reaction time of 2 hours at 290° C., the mixture in the flask was cooled and washed with 3.66 liter of a 3% ammonia solution, by mixing the reaction mixture and the solution and stirring the mixture and the solution for a couple of minutes. Then the diluted slurry of the combined mixture and solution was filtered, and the residual filter cake so obtained was dried. After filtering and drying, melam (241 grams, yield 100%) was obtained. The sulfur content was 0.5 wt. %. Hence, the para-toluene sulfonic acid content was 2.5 wt. %. Comparative experiment A is equal to example 2 of WO-96/16948.

Comparative Experiment B

A horizontally arranged double-walled stirred reactor with an effective capacity of 120 liters was heated via a thermostatically controlled oil-heated reactor jacket set at 350° C. The reactor was filled with melamine (37.2 kg) and para-toluene sulfonic acid (25.3 kg). The reactor was operated under a mild nitrogen overpressure (0.6 m3/h) in order to remove all ammonia formed in the condensation reaction. The temperature of the reactor contents was gradually raised to 300° C., after which the contents were allowed to cool. The total reaction time was 260 minutes of which approximately 60 minutes is spent for heating. The product was washed with 538 liter of a 3%° C. ammonia solution to yield melam by mixing the product and the solution. Then the diluted slurry of the combined mixture and solution was filtered, and the residual filter cake so obtained was dried. The melam was dried for 3 hours at a temperature of 175° C. to yield dry melam powder. 59.4 kg (yield 99.18) of dry melam powder was obtained with a paratoluene sulfonic acid content of 42 wt. %. Comparative experiment B is equal to example 3 of WO-96/16948.

Comparative Experiment C

Comparative experiment A was repeated. However after the heating step a slurry of the reaction mixture in 3.66 liter of a solution of sodium hydroxide in water, having a pH of 13 was made. The diluted slurry was stirred for 6 hours at a temperature of 50° C. Thereafter the diluted slurry was filtered and the cake of the concentrated slurry on the filter was washed with 12 liters of water. After drying 235 g of melam were obtained containing less than 0.08 wt. % of para-toluene sulphonic acid.

Comparative Experiment D

Comparative example C was repeated. However, after filtering the diluted slurry, the cake obtained was removed from the filter and diluted with the same amount of fresh water as the amount of obtained filtrate to obtain a new diluted slurry. The steps of filtering and reslurrying have been performed 3 times, each time collecting the filtrate in a separate beaker.

In total the amount of fresh water used was 10.9 L. After drying 235 g of melam were obtained containing less than 0.05 w % para toluenesulphonic acid.

Comparative Experiment E

Comparative experiment B was repeated, however after the heating step a slurry of the reaction mixture in 538 liter of a solution of sodium hydroxide in water, having a pH of 13 was made. The diluted slurry was stirred for 6 hours at a temperature of 50°

Prior to drying the slurry was filtered and the cake obtained was diluted with 538 L of fresh water to yield the initial volume. Filtrates were each collected in separate tanks. The filtration and cake dilution step was repeated 3 times after which the cake was dried and 34.1 kg of dry melam was obtained. The total amount of fresh water used was 2155 L. The content of paratoluene sulfonic acid in the so obtained final mixture was less than 0.05 w %.

Example 1

Comparative example D was repeated several times, however, during each repetition the 3 washing steps, each comprising filtering and reslurrying, have been performed using the beakers with the collected filtrates from a previous repetition of this example 1 where the beaker with filtrate of step x from the previous repetition was used for step x−1. In the last washing step a portion of fresh water has been used.

In total the amount of fresh water used per repetition was 4.1 L. After drying 235 g of melam were obtained containing less than 0.05 w % para toluenesulphonic acid.

Example 2

Comparative example E was repeated several times, however, during each repetition the 3 washing steps, each comprising filtering and reslurrying, have been performed using the tanks with the collected filtrates from a previous repetition of example 2 where the tank with filtrate of step x of the previous repetition was used for step x−1. In the last washing step a portion of fresh water has been used.

In total the amount of fresh water used per repetition was 550 L. After drying 34.0 kg of melam were obtained containing less than 0.05 w % para toluenesulphonic acid.

The following table shows some typical values for the relative amount of wash liquid requirements, needed to achieve a comparable high level of purity, for different washing conditions.

TABLE 1

| Example/Comparative experiment | amount of water needed (liter fresh water/kg purified product) | remaining pTSA (wt %) |
| --- | --- | --- |
| Comparative experiment A | n.a. | 2.5 |
| Comparative experiment B | n.a. | 42 |
| Comparative experiment C | 51.1 | 0.08 |
| Comparative experiment D | 46.4 | <0.05 |
| Comparative experiment E | 63.2 | <0.05 |
| Example 1 | 17.4 | <0.05 |
| Example 2 | 16.2 | <0.05 |

Because of the high cake resistance of melam in dead-end filtration the wash liquid flux per unit cake volume is very low. This results in very long filtration times and/or unpractical large filter surface requirements.

It is noted that the low wash water volumes are furthermore achieved because of the special initial preparation of the diluted slurries in combination with the specified washing methods. Decanting centrifuge is most preferred because of low volumes of wash liquid used and the absence of cakes blocking filtration or due to crack formation.

The invention claimed is:

1. A process for the purification of a melamine condensation product obtained by a process comprising the step of heating a starting material comprising melamine or a melamine salt in the presence of:
   (i) at least one organic or inorganic acid, or
   (ii) at least one ammonia or melamine salt of the acid, or
   (iii) a combination of (i) and (ii),
   under reaction conditions effective for the formation of a melamine condensation product, resulting in a reaction product mixture comprising melamine condensation product and the organic or inorganic acid and/or salts or other residues thereof, wherein
   the purification process comprises the steps of:
   (a) making a diluted slurry of the reaction product mixture in a solution of a base in water with a pH of at least 9,
   (b) keeping the diluted slurry for a period of at least 1 hour,
   (c) concentrating the diluted slurry, thereby obtaining a concentrated slurry and an eluent, and
   (d) washing the concentrated slurry by diluting the concentrated slurry with aquous liquid and repeating step c, wherein
   the washing step (d) is performed by counterflow washing using eluents of downstream concentration steps to wash the slurry in upstream concentration steps.

2. The process according to claim 1, wherein the washing of the concentrated slurry according to step (d) is carried out in N washing steps, with N being a positive integer, wherein in step n1=x, x being an integer from 1 up to and including N−1, and wherein the mixture is washed with water used in step n2=x+1, and wherein in step n3=N the condensation product is washed with a fresh aqueous liquid.

3. The process according to claim 2, wherein N is an integer in the range of 2-10.

4. The process according to claim 1, wherein less than 50 liters of aqueous solution per kg of purified condensation product is used.

5. The process according to claim 1, further comprising the conducting filtration by dead end filtration combined with counterflow washing.

6. The process according to claim 1, wherein the amount of base is at least in a stochiometric amount with the acid in the reaction product mixture.

7. The process according to claim 1, wherein the base is sodium hydroxide.

8. The process according to claim 1, wherein step (b) is carried out at a temperature of 20-70° C.

9. The process according to claim 1, wherein step (b) is carried out for a period of at most 14 hours.

10. The process according to claim 1, wherein step (b) is carried out in a stirred vessel.

11. The process according to claim 2, wherein the fresh aqueous liquid is water.

* * * * *